United States Patent [19]

Durette

[11] Patent Number: 4,923,852

[45] Date of Patent: May 8, 1990

[54] AMINOALKYL NAPHTHALENEDIOLS AS HOST RESISTANCE ENHANCERS AGAINST VIRAL INFECTIONS

[75] Inventor: Philippe L. Durette, New Providence, N.J.

[73] Assignee: Merck & Co., Inc., Rahway, N.J.

[21] Appl. No.: 60,209

[22] Filed: Jun. 11, 1987

[51] Int. Cl.$^5$ .................. A61K 31/70; A61K 31/505; A61K 31/33

[52] U.S. Cl. ...................... 514/49; 514/459; 514/472; 514/652; 514/42; 514/450; 514/552

[58] Field of Search .................. 514/459, 472, 655, 2, 514/42, 49, 450, 552; 424/85.2, 85.4, 85.5, 85.6, 85.7

[56] References Cited

U.S. PATENT DOCUMENTS 3,004,069  10/1961  Duffin ............................. 564/387
3,009,912  11/1961  Duffin ............................. 564/387

FOREIGN PATENT DOCUMENTS 790202  2/1958  United Kingdom .
790203  2/1958  United Kingdom .

OTHER PUBLICATIONS

Sandstrom, Drugs, vol. 31, pp. 463–466, 1986.
British Journal of Pharm. vol. 12, pp. 171–175 (1957).
Synthetic Immunostimulants in Antitumor Therapy—Drugs of the Future, vol. 8, pp. 615–638 (1983).
Immunomodulators in the Immunotherapy of Cancer and Other Diseases—Trends in Pharmacological Sciences (TIPS), pp. 191–194 (1982).
The Experimental and Clinical Use of Immunomodulating Drugs in the Prophylaxis and Treatment of Infections—Infection vol. 12, p. 1957 (1984).

Primary Examiner—Blondel Hazel
Attorney, Agent, or Firm—John W. Harbour; Robert J. North; Charles M. Caruso

[57] ABSTRACT

Disclosed are specific aminoalkyl naphthalenediol derivatives that enhance natural human host resistance to viral infectious organisms and particularly AIDS-related viruses. Such agents are also administered prophylactically to individuals whose resistance to infection has been specifically immunocompromised by an AIDS-related (HIV) virus.

3 Claims, No Drawings

# AMINOALKYL NAPHTHALENEDIOLS AS HOST RESISTANCE ENHANCERS AGAINST VIRAL INFECTIONS

BACKGROUND OF THE INVENTION

1. Field of the Invention

The present invention relates to certain aminoalkyl naphthalenediol derivatives that enhance natural human host resistance to viral infectious organisms. The derivatives are administered prophylactically to human individuals whose resistance to infection has been compromised by chemotherapy, surgery, burns, other forms of severe stress, and, in particular, AIDS-related virus.

2. Brief Description of Disclosures in the Art

Recent medical progress has resulted in beneficial therapy for many patients with conditions which were previously untreatable. As a result of both the extended survival of such patients and the therapeutic methods employed, today's physicians are more frequently encountering the patient who is at great risk of developing opportunistic infection because his host defenses have been impaired in particular by an AIDS-related virus.

Seven years ago few had ever heard of acquired immunodeficiency syndrome, or AIDS. This puzzling affliction, then seen in only a small number of young, homosexual men, was something new and unnamed. Today, it's hard to find anyone in the U.S. who hasn't heard of AIDS, the disease that can debilitate and then kill its victim with horrific swiftness.

AIDS has come to be recognized as a public health emergency. More than 27,700 American men, women, and children have been stricken by it; the death toll is 16,000 and rising. The U.S. Public Health Service predicts that by the end of 1991 more than 179,000 persons will have succumbed to the disease.

Thus far, there is no cure for AIDS.

Technically, Acquired ImmuneDeficiency Syndrome (AIDS) is a transmissible deficiency of cellular immunity characterized by opportunistic infections and certain rare malignancies. The dominant risk groups for AIDS include homosexually active males, intravenous drug abusers, recipients of transfusions and blood products, and the heterosexual partners and children of high-risk individuals, suggesting the involvement of an infectious agent transmitted through intimate contact or blood products.

Recent evidence indicates that the infectious agent responsible for disease transmission is a novel lymphotropic retrovirus, currently designated HIV (human immunodeficiency virus) and also known as lymphadenopathy-associated virus (LAV) (Barré-Sinoussi et al., *Science* 220: 868 (1983)). Similar viruses have been reported by other scientific groups (Popovic et al., *Science* 224: 497 (1984); Levy et al. *Science* 225: 840 (1984)) and designated human T-cell lymphotropic virus type III (HTLV-III), AIDS-associated retrovirus (ARV), or immunedeficiency-associated virus (IDAV). Still more recent data indicates that LAV, HTLV-III, ARV and IDAV share several important characteristics, including substantial nucleotide homology (Wain-Hobson et al., *Cell* 40: 9 (1985); Muesing et al., *Nature* 313: 450 (1985); Sanchez-Pescador et al., *Science* 227: 484 (1985)), and should be considered isolates of the same virus, although there is a likelihood that strain-to-strain variations among the viral isolates will exist. In addition to exhibiting substantial nucleotide homology, the isolates are similar with respect to morphology, cytopathology, requirements for optimum reverse transcriptase activity, and at least some antigenic properties (Levy, suora: Schupbach et al., *Science* 224: 503 (1984)). The above materials are hereby incorporated by reference to characterize the phrase "AIDS-related virus".

In the field of immunology, it has been found that certain compounds including, bacterial cell wall peptidoglycans (in particular, muramyl dipeptide and its derivatives) lipopolysaccharide, glucans, ubiquinones, bestatin, amphotericin B, tuftsin, thymic hormones, interferon, polyadenylic acid complexes, pyran copolymers, levamisole, methisoprinol and the like, although not specifically therapeutic against a particular pathogen, act in such a manner to improve the host resistance to infection by bacteria, virus, fungus, or parasite in a human host whose immunological system has been compromised.

In the past, bacterial cell wall products (e.g., BCG, *C. parvum*, etc.), as well as plant polysaccharides (e.g., lentinan, krestin, etc.), have been employed to stimulate the natural host resistance. These agents all suffer from undesirable toxic side effects, such as granulomatous inflammation, etc. Presumably the development of inflammation enhances the mobilization and activation of inflammatory cells as well as augmentation of the immune response (adjuvant effect).

In light of the above discussion, new classes of organic compounds are constantly being evaluated and screened to see if they possess host resistance enhancement activity, particularly in an immunocompromised host as a result of an AIDS-related virus.

One class of compounds recently of interest are the aminoalkyl naphthalenediols.

In the art, naphthalenediols are described in U.S. Pat. No. 3,009,912; British Pat. Nos. 790,203; 790,202; and in *Brit. J. Pharmacol.* 12(1957) p. 171, "Anti-Malarial Activity of Hydroxy-Substituted Naphthalene Compounds" by W. M. Duffin and I. M. Rollo. The above compounds are described as being active as antimalarial agents against blood forms of Plasmodium species. However, there is no specific suggestion as to their use as host resistance enhancement agents.

At present, there is no effective host resistance enhancer on the market that does not possess the ability to cause intense granulomatous inflammation. The use of host resistance compounds that cause inflammation is not desirable.

For reviews, see (1) J. Kralovec, "Synthetic Immunostimulants in Antitumor Therapy," *Drugs of the Future* 8(1983)615; (2) J. W. Hadden, "Immunomodulators in the Immunotherapy of Cancer and Other Diseases," *Trends in Pharmacological Sciences*, (1982)191; (3) E. Arrigoni-Martelli, "Developments in Drugs Enhancing the Immune Response," *Meth. Find. Exptl. Clin. Pharmacol*, 3(1981)247; and (4) J. Drews, "The Experimental and Clinical Use of Immunomodulating Drugs in the Prophylaxis and Treatment of Infections," *Infection*, 12(1984)157.

Therefore, it is an object of this invention to provide compositions containing host resistance enhancement agents that are safe and effective against viral infection and whose therapeutic mechanism does not involve significant granulomatous inflammation.

Furthermore, it is also an object of this invention to provide a method of treatment for enhancing host resistance against opportunistic infection in humans who are immunologically compromised as a result of an AIDS-related virus.

Further provided is a pharmaceutical composition comprising said agent and an approved AIDS therapeutic drug, e.g. azidothymidine (AZT).

SUMMARY OF THE INVENTION

It has been found that certain aminoalkyl naphthalenediol derivatives do in fact possess excellent activity as host resistance enhancing agents without causing significant granulomatous inflammation as a side effect. Further, the advantages are that the said compounds are non-pyrogenic and they do not sensitize the host to endotoxin.

By this invention there is provided a method for enhancing resistance against viral infection in a human immunocompromised host, comprising administering to said host a composition comprising a compound of the formula:

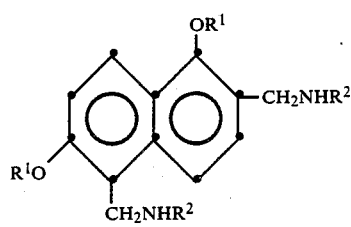

where $R^1$ is independently selected from H, $C_1-C_6$ alkyl; $R^2$ is independently selected from substituted monocycloalkyl or unsubstituted or substituted di- or tri- cycloalkyl, or heterocycloalkyl, or pharmaceutically acceptable acid addition salts thereof, in a pharmaceutically acceptable medium, in an amount effective to impart resistance against viral infection.

Also provided is a method for enhancing the host resistance against opportunistic bacterial, fungal or viral infection in a human host immunologically compromised by an AIDS-related virus, comprising administering to said host the above-described pharmaceutical composition, in combination, concurrently or separately, with an anti-AIDS therapeutic drug.

Furthermore, there is provided composition for enhancing host resistance against bacterial, fungal or viral infection in a human host immunocompromised by an AIDS-related virus comprising a compound of the formula:

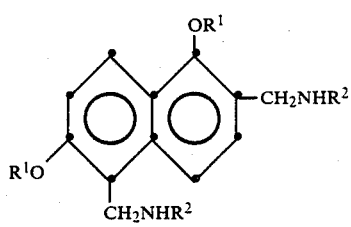

where $R^1$ is independently selected from H, $C_1-C_6$ alkyl; $R^2$ is independently selected from substituted monocycloalkyl, unsubstituted or substituted di- or tri- cycloalkyl, or heterocycloalkyl, or pharmaceutically acceptable acid addition salts thereof, in combination with an anti-AIDS drug, in a physiologically acceptable medium in an amount effective to impart enhanced resistance against opportunistic infection.

Specifically provided is where the composition contains an anti-AIDS drug is selected from one or more of the following: azidothymidine, AL 721, ampligen, ansamycin, azimexon, cyclosporine, foscarnet, HPA-23, imreg-1, inosine pranobex, alpha-interferon, interleukin-2, D-penicillamine, ribavirin, suramin, CS-85, 2',3'-dideoxycytidine, 2',3'-dideoxyadenosine, gamma interferon, RNA deriv, Immune globulin IG-IV, thymopentin, thymostimulin, methionine-enkephalin or equivalents thereof.

DETAILED DESCRIPTION OF THE INVENTION AND PREFERRED EMBODIMENTS

By the term "AIDS-related virus" is meant the commonly designated HIV series (human immunodeficiency virus) formerly called HTLV and LAV, and species thereof, as described above in the indicated incorporated references.

The compounds of the present invention may be prepared by reacting the appropriate naphthalenediol with formaldehyde and the appropriate amine, $R^2NH_2$, in a suitable solvent such as methanol; the reagents will react on standing or may be heated together. The product of this reaction is a bis-oxazine compound. A 1,3-oxazine ring is formed on each side of the naphthalene ring by condensation of the naphthalenediol with 4 molar equivalents of formaldehyde in the presence of two equivalents of $R^2NH_2$:

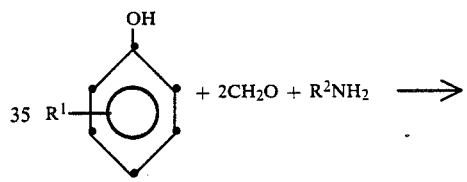

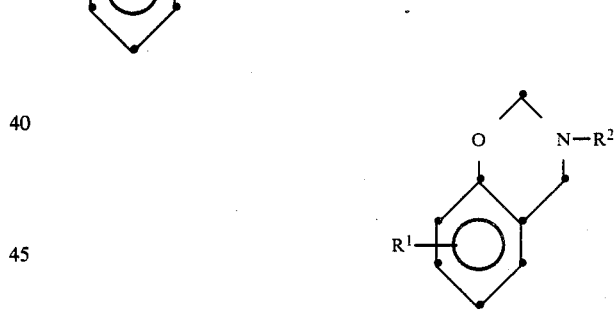

The oxazine rings can be opened by acid hydrolytic methods and the formaldehyde removed in a manner to be described below.

As an example, the following sequence of formulae illustrates the preparation of the compound 2,5-bis(-trans-4-methylcyclohexylaminomethyl)naphthalene-1,6-diol, which is a preferred compound:

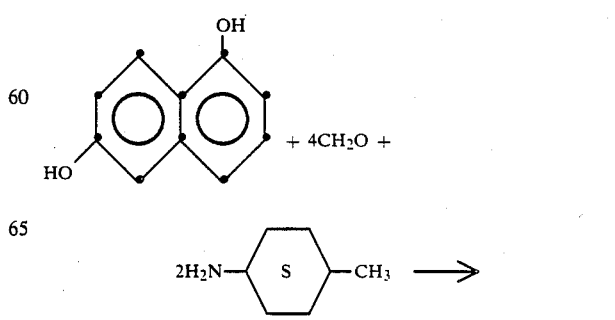

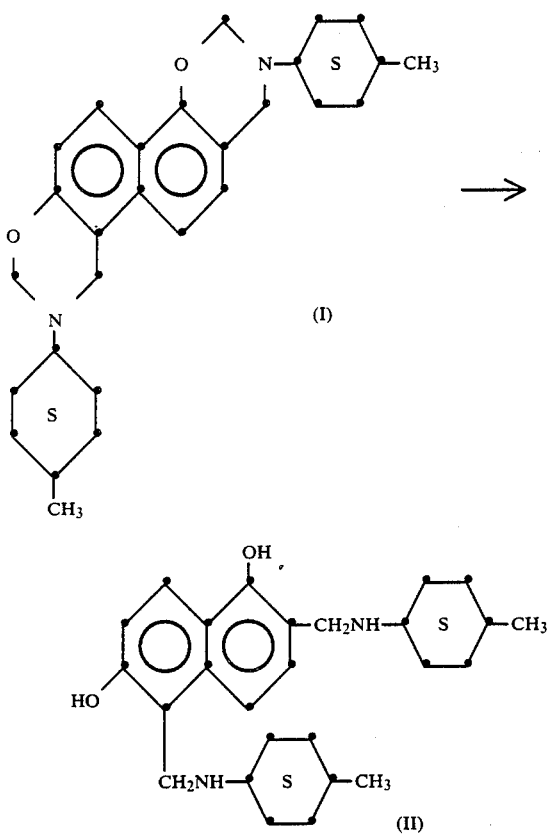

The opening of the oxazine rings in a compound of the type in Formula I, resulting in a compound of Formula II, may be carried out by treating I with an acid in an aqueous alcohol system, such as aqueous ethanol or aqueous isopropanol. For this purpose, 10% hydrochloric acid or 2 N sulphuric acid is convenient. The reaction may also be carried out in the cold in the presence of a compound such as 2,4-dinitrophenylhydrazine which will react with formaldehyde as it is formed; this prevents loss of material due to polymerization.

Preparation of the 1,6-dialkoxy compounds, which include alkoxy groups of $C_1$ to $C_6$ alkyl, which can be linear or branched, generally involves dissolving the 1,6-dihydroxy compound, wherein the amino functionalities are protected, such as their benzylcarbamates, in a suitable solvent such as tetrahydrofuran, 1,4-dioxane, N,N-dimethylformamide, dimethylsulfoxide, hexamethylphosphorictriamide, or the like, adding base such as sodium hydride, or the like, to create the phenoxide salt and adding a suitable alkylating agent such as iodomethane, bromoethane, or the like, in sufficient quantity being at least 2 molar equivalents such that the dialkoxy compound in the 1,6-positions is formed, removal of the amino protecting groups, such as by hydrogenolysis, and, finally, generation of the bis hydrochloride salt by treatment with aqueous HCl.

Representative classes of $R^2$ groups are chosen from cycloaliphatic, heterocycloaliphatic and their $C_1$–$C_6$ alkoxy derivatives.

Representative examples of $R^2$ include 1-adamantyl, 2-adamantyl, 3-methyl-1-adamantyl, 3-methyl-2-adamantyl, 3,5-dimethyl-1-adamantyl, 3,5-dimethyl-2-adamantyl, 3-ethyl-1-adamantyl, 3-ethyl-2-adamantyl, 3-propyl-1-adamantyl, 3-propyl-5-ethyl-adamantyl, 3-t-butyl-2-adamantyl, 3-isopropyl-1-adamantyl, 3-methoxy-1-adamantyl, 3-ethoxy-1-adamantyl, 3-propoxy-1-adamantyl, 1-adamantylmethyl, 2-adamantylmethyl, 3-methyl-1-adamantylmethyl, 3-methyl-2-adamantylmethyl, 3,5-dimethyl-1-adamantyl-methyl-, 3-ethyl-1-adamantylmethyl-, 3-propyl-1-adamantylmethyl, 3,5-dimethyl-2-adamantyl, 3-methoxy-1-adamantylmethyl, 3-ethoxy-1-adamantylmethyl, 3-ethyl-5-methoxy-1-adamantyl, cyclohexyl, 2-,3-, or 4-monomethylcyclohexyl (both cis & trans-isomers), 2,4-dimethylcyclohexyl, 2,4,6-trimethylcyclohexyl, 4-t-butyl, 2-propylcyclohexyl, 3-propylcyclohexyl, 4-propylcyclohexyl, 4-t-butylcyclohexyl, 4-secbutylcyclohexyl, 2,3, or 4-methoxycyclohexyl, 4-ethoxycyclohexyl, 4-propoxycyclohexyl, 4-butoxy-cyclohexyl, cyclohexylmethyl-, 2-,3-,4-trimethylcyclohexylmethyl-, 2,4-dimethylcyclohexylmethyl-, 2-methoxycyclohexylmethyl-, 4-t-butoxycyclohexylmethyl-, 3-isopropoxycyclohexylmethyl-, 4-tetrahydropyranyl-, 3-tetrahydropyranyl, 2-tetrahydropyranyl, 2-methyl-4-tetrahydropyranyl, 3-methyl-4-tetrahydropyranyl, 2,5-dimethyltetrahydro-4-pyranyl, 2-methoxy-tetrahydro-4-pyranyl, 2,6-dimethoxytetrahydro-4-pyranyl, tetrahydropyranyl-4-methyl, 2-methyltetrahydropyranyl-4-methyl, 2,5-dimethoxytetrahydropyranyl-4-methyl; cyclopentyl, cyclopentylmethyl or substituted cyclopentyl, similarly as with cyclohexyl; cycloheptyl or substituted cycloheptyl, similarly as with cyclohexyl; exo or endo-norbornyl, tetrahydrofurfuryl, and the like, and cis and trans isomers thereof.

Utilizing amine with the above described $R^2$ radicals for synthesis of the subject compounds and their oxazines, the compounds listed in the following table were synthesized.

TABLE

| Compound | $R^1$ | $R^2$ |
|---|---|---|
| 1 | H | 1-Adamantyl |
| 2 | H | 2-Adamantyl |
| 3 | H | cyclohexylmethyl |
| 4 | H | exo-2-norbornyl |
| 5 | H | 4-tert-butylcyclohexyl (cis and trans) |
| 6 | H | tetrahydrofurfuryl |
| 7 | H | 2-methylcyclohexyl |
| 8 | H | 3-methylcyclohexyl |
| 9 | H | 4-methylcyclohexyl (cis) |
| 10 | H | 4-methylcyclohexyl (trans) |
| 11 | H | cyclopentylmethyl |
| 12 | H | 4-methoxycyclohexyl |
| 13 | H | 2-methylcyclopentyl (trans) |
| 14 | H | tetrahydro-4H-pyran-4-yl |
| 15 | $CH_3$ | cyclohexyl |
| 16 | $(CH_2)_3CH_3$ | cyclohexyl |

The compounds in the present invention possess immunostimulatory properties and may be used as immunomodulating agents, i.e. to stimulate the host immune response. They are especially useful for increasing the human host response against viral infections in humans, immunocompromised by chemotherapy, surgery, burns and severe stress.

These compounds are especially useful in the case of herpesviridae, picorna-viridae and myxo viruses, but also in the case of mastadeno viruses, such as, especially, human adeno viruses, in the case of chordopoxvirinae, such as, chiefly, orthopox viruses, such as, especially, for example, vaccinia viruses, in the case of reoviridae, above all (especially human) rota viruses, and in the case of caliciviridae and rhabdoviridae, such as, especially, vesiculo viruses in humans.

These compounds of the formula I are used chiefly in the case of alpha-herpesvirinae, such as varicella viruses, for example human varicella-zoster viruses, rhino viruses, cardio viruses and orthomyxoviridae, but also in the case of beta-herpesvirinae, such as, especially, human cytomegaloviruses, and in the case of para-myxoviridae, such as, especially, pneumo viruses, for example respiratory syncytial viruses in humans, and such as, also, morbilli viruses or para-myxo viruses, such as para-influenza viruses, for example human parainfluenza viruses, including Sendai viruses, and in the case of arbo viruses or vesiculo viruses, for example Vesicular stomatitis viruses.

These compounds are used very especially in the case of simplex viruses, for example human Herpes simplex viruses of types 1 and 2, in the case of human encephalomyocarditis viruses, in the case of influenza viruses, such as, especially, influenza A and influenza B viruses, in the case of vaccinia and para-influenza viruses and very especially in the case of the viruses mentioned in the Examples.

These compounds can be used for the prophylaxis and treatment of virus infections, by administering them enterally or parenterally, especially together with suitable adjuncts or carriers. They are preferably applied to the mucous membranes, for example intranasally, rectally or vaginally, or to the conjunctiva of the eye, or orally. However, the antiviral effect also occurs in the case of administration by other routes, for example subcutaneously, intravenously or intramuscularly, or in the case of application to normal skin.

The dosage of the active ingredient depends, inter alia, on the particular human's resistance, the method of administration and the type of virus. There is relatively little relationship between the dosage and the effect.

For prevention, a single dose of from approximately 1 mg/kg to approximately 50 mg/kg of body weight, preferably from 175 to 2800 mg, for example 500 mg, of active ingredient is administered to a human of approximately 70 kg body weight. The Prophylactic effect of this dose lasts for several days. If necessary, for example, when there is an increased risk of infection, the administration of this dose can be repeated.

The therapeutic dose for humans of approximately 70 kg body weight is from 70 mg to 3500 mg, preferably from 175 to 2800 mg, for example 500 mg, especially in the case of oral administration. The dose in the case of topical, especially intranasal, administration is up to ten times lower. If necessary, the administration of these compounds of the formula I can be repeated until there is an improvement in the illness. Often, however, a single administration is sufficient.

The pharmaceutically acceptable compounds of the present invention can be used, for example, for the manufacture of pharmaceutical preparations that contain a pharmaceutically effective amount, for example an amount sufficient for immunostimulation, of the active ingredient together or in admixture with a significant amount of inorganic or organic, solid or liquid pharmaceutically acceptable carriers.

The pharmaceutical preparations according to the invention are for enteral, such as oral or rectal, and parenteral, such as intraperitoneal, intramuscular or intravenous, administration to warm-blooded animals and contain the pharmacological active ingredient alone or together with a pharmaceutically acceptable carrier.

The carriers may be inorganic or organic and solid or liquid. For example, there are used tablets or gelatine capsules that contain the active ingredient together with diluents, for example lactose, dextrose, sucrose, mannitol, sorbitol, cellulose and/or glycerine, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat or rice starch, gelatine, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colorings, flavorings and sweeteners. The pharmacologically active compounds of the present invention can also be used in the form of parenterally administrable preparations or in the form of infusion solutions. Such solutions are preferably isotonic aqueous solutions or suspensions, it being possible, for example in the case of lyophilized preparations that contain the active ingredient alone or together with a carrier, for example mannitol, for these to be manufactured before use. The mentioned solutions or suspensions may contain viscosity-increasing substances, such as sodium carboxymethylcellulose, carboxymethylcellulose, dextran, polyvinylpyrrolidone or gelatine. The pharmaceutical preparations may be sterilized and/or contain adjuncts, for example preservatives, stabilizers, wetting agents and/or emulsifiers, solubilizers, salts for regulating the osmotic pressure and/or buffers. The present pharmaceutical preparations which, if desired, may contain other pharmacologically active ingredients, such as antibiotics, are manufactured in a manner known per se, for example by means of conventional mixing, granulating, confectioning, dissolving or lyophilizing processes, and contain approximately from 0.001% to 99%, especially from approximately 0.01% to approximately 10%, more especially from 0.1% to 5%, of the active ingredient(s), an active ingredient concentration of less than 1% being especially suitable for preparations that are to be applied topically.

Pharmaceutical preparations according to the invention may be, for example, in dosage unit form, such as dragees, tablets, capsules, suppositories or ampoules.

Pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragee cores. It is also possible to incorporate them into synthetic carriers that release the active ingredients, or allow them to diffuse, in a controlled manner.

The manufacture of injection preparations is carried out in customary manner under antimicrobial conditions, as is the filling into ampoules or phials and the sealing of the containers.

Furthermore, the compounds of the present invention provide, in combination with "anti-AIDS drugs", human host protection against opportunistic infections, in individuals immunocompromised by an AIDS-related infectious organism. These "opportunistic infections" as used herein include fungal, viral, and bacterial, including, the specific condition pneumocystis pneumonia. They are also capable of potentiating antibiotic activity.

By the term "anti-AIDS drugs" is meant therapeutic drugs which are thought to act directly or indirectly against the AIDS-related virus by a variety of known or unknown mechanisms, i.e. antiviral or immunomodulating mechanisms.

The following anti-AIDS drugs are currently being investigated and are known to exhibit either some antiviral or immunomodulating effect in a human host against the AIDS-related virus (from Chemical & Engineering News, December 8, 1986, pp 7-14, hereby incorporated by reference for this purpose):

AL 721. Lipid mixture composed of neutral glycerides, phosphatidylcholine, and phosphatidylethanolamine in 7:2:1 ratio. Interferes with HIV infectivity but not by inhibiting reverse transcriptase; possibly it disrupts the virus's membrane. No adverse effects observed during a six-week clinical trial.

Ampligen. Mismatched double-stranded RNA polynucleotide that induces the body to release interferon, thus stimulating antiviral activity. Reportedly does not have side effects of interferon injections. Currently undergoing preliminary clinical trials in AIDS patients.

Ansamycin (rifabutin, $C_{45}H_{29}N_4O_{11}$). Italian antibacterial drug, a member of the rifamycin group of antibiotics, which are characterized by a natural ansa structure (chromophoric naphthohydroquinone group spanned by a long aliphatic bridge). Drug has shown some efficacy in treating AIDS patients with an opportunistic infection caused by the bacterium Mycobacterium aviumintracellulare.

Azidothymidine (AZT, 3'-azido-3'-deoxythymidine). First drug to show promise in prolonging lives of patients with AIDS or AIDS-related complex (ARC). Well absorbed orally and effectively penetrates central nervous system, but has relatively short half-life in the body and some toxicity, with anemia and headaches. ARC patients treated with AZT showed virtually no toxic effects.

Azimexon. Cyanaziridinyl immunomodulator. Early trial showed improvements in symptoms and immune function in patients with ARC but not AIDS; only toxic effect was mild hemolysis (disintegration of red blood cells with release of hemoglobin), which disappeared when treatment ceased.

Cyclosporine (cyclosporin A). Cyclic oligopeptide with potent immunosuppressive effects. Inhibits T4 lymphocyte-dependent immune responses. Basis of controversial AIDS therapy in France; rationale is that HIV infects "activated" T4 cells, which are primed to defend that body, so drug that prevents activation of T4 cells may limit progression of disease. The French claim encouraging results with it.

Foscarnet (trisodium phosphonoformate). Swedish drug that has been used to treat CMV infection in immunocompromised patients, also to treat herpes. Inhibits HIV reverse transcriptase activity in vitro at levels pharmacologically acceptable in vivo. Formulation problems and serious side effects have been encountered. No results yet reported in HIV-infected patients.

HPA-23 (ammonium 21-tungsto-9-antimoniate, $[(NH_4)_{18}(NaW_{21}Sb_9O_{86})_{17}]$. Inhibits reverse transcriptase in several retroviruses in vitro, but mechanism of antiviral action against HIV is unknown. Drug has shown some tendency to check the growth of HIV, but no therapeutic benefit has been documented in AIDS patients.

Imreg-1. Proprietary immunomodulator derived from white blood cells. Reportedly can enhance production of other biological response modifiers such as interleukin-2 and $\gamma$-interferon, which are critical to normal functioning of immune system.

Inosine pranobex (isoprinosine, inosiplex). p-Acetamidobenzoic acid salt of dimethylaminoisopropanol: inosinate complex, 3:1 molar ratio. Chemically synthesized antiviral and immune modulator originally developed to enhance memory in elderly. In one study, found to improve immune function in ARC patients.

$\alpha$-Interferon. Glycoprotein produced by cells in response to virus infection; helps amplify or regulate immune responses. Checks the growth of HIV in vitro. Has induced tumor regression in some AIDS-related Kaposi's sarcoma cases. Not known whether $\alpha$-interferon has anti-HIV activity in vivo.

Interleukin-2 (IL-2). Protein made by white blood cells that mediates production of interferon. Inability to produce IL-2 may predispose AIDS patients to opportunistic infections. Preliminary results of therapy with recombinant IL-2 not encouraging, but trials continue.

D-Penicillamine (3-mercapto-D-valine). Used to treat rheumatoid arthritis and Wilson's disease, a rare copper-storage disease. Inhibits HIV reproduction in humans. In trials at George Washington University Medical Center, it suppressed the virus but also temporarily depressed T cell levels in 13 AIDS patients with perpetually swollen glands.

Ribavirin (1-$\beta$-D-ribofuranosyl-1,2,4-triazole-3-carboxamide). Synthetic nucleoside used to treat a viral respiratory infection in children. In early clinical trials, it inhibited viral replication and improved immune function in AIDS patients. Longer (24-week) trial in 373 ARC patients was completed last month; at 12 weeks, ribavirin's safety profile was judged to be acceptable, and the drug was found to be well tolerated. Final results will be available soon.

Suramin ($C_{51}H_{34}Na_6O_{23}S_6$). Antiparasitic agent. Potent inhibitor of HIV reverse transcriptase, but also significantly inhibits desirable biological functions. In AIDS patients, it has produced little or no evidence of clinical improvement or immunologic recovery. Has serious side effects, inability to penetrate central nervous system. Not considered appropriate for single-agent use in AIDS. No longer being actively pursued.

Furthermore, the US Food and Drug Administration has released a list of 16 proposed AIDS treatments which have received IND status. The list contains only treatments which "have been publicly acknowledged by their sponsors", and therefore some experimental treatments may have been omitted.

| Experimental treatment | Sponsor |
|---|---|
| Immunomodulators | |
| Thymopentin | Ortho Pharmaceuticals |
| Thymostimulin | Serono Laboratories |
| Methionine-enkephalin | National Jewish Hospital |
| Isoprinosine | Newport Pharmaceuticals |
| Antivirals | |
| Ansamycin | Adria Laboratories |
| Ribavirin | Viratek/ICN Pharmaceuticals |
| Dideoxycytidine (DDC) | National Cancer Institute |
| HPA-23 | Rhone-Poulenc |
| AL-721 | Matrix Laboratories[1] |
| Foscarnet | National Institute of Allergy and Infectious Diseases[2] |
| Biologicals | |
| Alpha-interferon | Hoffmann-La Roche |
| Gamma-interferon | Genentech |
| Imreg-1 | Imreg Inc |
| Interleukin-2 | Hoffmann-La Roche |
| RNA deriv | HEM Research |
| Immune globulin IG-IV | Sandoz Pharmaceuticals and Alpha Therapeutics |

[1] a subsidiary of Praxis Pharmaceutical;

Further, Yakult's immunostimulant, LC-9018, and two herbal products, shosaikoto and ginseng, being studied by Tsumura Juntendo, may be of benefit in patients with AIDS, according to a recent note from Jardine Fleming analysts (Japan).

LC-9018 has been found to be about 20 times more potent than Ajinomoto's lentinan in inducing macrophage activation, and it will soon enter clinical trials in AIDS patients in the US, note the analysts. Phase III trials with LC-9018 in patients with cancer are currently underway in Japan, they add. Shosaikoto and ginseng have been found to increase depleted helper T-cell counts in seven of nine AIDS-carriers studied by researchers at Tsumura Juntendo and Tokyo Medical University, the Jardine Fleming analysts note.

Furthermore, HEM Research's potential anticancer agent, ampligen (a mismatched doublestranded RNA), reduces at least five-fold the concentration of Wellcome's zidovudine (Retrovir) required for inhibitory activity against human immunodeficiency virus (HIV) in vitro, according to US researchers writing in The Lancet (April 18th, p 890). Ampligen is currently in Phase II clinical trials as an anticancer agent and HEM is seeking partners to fund a clinical trial in AIDS.

At higher concentrations of zidovudine, there seemed to be a synergistic relation between the two compounds, since complete protection was provided by combined suboptimal doses of each drug, the authors note. They predict that ampligen would reduce the dose of zidovudine required for a therapeutic effect in vivo, so reducing its toxicity.

Since the two drugs have entirely different modes of action, it is unlikely that they will exert toxicities other than those associated with each drug alone, the researchers comment. In recent clinical studies, "virtually no toxicity" was associated with intravenous ampligen, they add. Moreover, since ampligen has clinically demonstrated immunological as well as antiviral activity, its use together with zidovudine may have pronounced and long-term beneficial effects on the course of AIDS beyond that which can be estimated in vitro, they conclude.

In addition, CS-85, or 3'-azido-2',3'-dideoxy-5-ethyluridine developed by Raymond F. Schinozi at the Veterans Administration Medical Center and Emory University, both in Atlanta, Georgia, shows promise.

All of the above-described compounds are deemed to be included within the scope of the term "anti-AIDS drug" as used herein. Use of more than one of these compounds, in addition to the naphthalenediol, in the combination composition is contemplated.

The composition containing the naphthalenediol compounds and an above-described anti-AIDS drug will contain the diol in an amount as to 3:1 described above and the anti-AIDS drug in an amount, based on the diol, in a weight ratio of 1:3 and preferably 1:1 based on the weight of diol.

The dosage form of the combination drug will be 1 to 50 mg/kg of human body weight per day and preferably 2.5 to 40 mg/kg.

The method of co-administering the two ingredients, if not using the combination composition, can be separately, concurrently or simultaneously.

The obtained compounds can be transformed to their salts in a classical fashion, for example, by reacting the acidic compounds obtained with alkaline or alkaline earth hydroxides or the basic compounds with acids.

The present invention is also directed to pharmaceutical preparations that contain a compound of Formula II. Among the pharmaceutical preparations relevant to this invention are salts that are administered by external route, for example, orally, rectally or parenterally to human species. Preparations may be administered that contain the pharmacologically active compound by itself or mixed with a pharmacologically acceptable carrier. The dose of the pharmacologically active compound depends on the sex, the age, and the state of the human individual and the mode of application.

The new pharmaceutical preparations contain from about 10% to about 95% and, preferably from about 20% to about 90% of a compound of the present invention. The pharmaceutical preparation relevant to this invention can be presented, for example, in the form of unit doses like tablets, capsules, suppositories, and ampoules.

The immunostimulatory properties of the compounds in the present invention can be demonstrated with the following protocols:

1. Compatibility

Although the compounds of the present invention produce their stimulatory effect with guinea pigs, for example, beginning with a single dose of 0.05 mg/kg s.c., and with mice after 5 applications of 10 mg/kg s.c., no toxic effect is observed after 5 applications of 300 mg/kg i.p., with the mouse. These compounds possess, therefore, a remarkable therapeutic index.

The compounds of the present invention thus have the capacity, on the one hand, of being mixed with an antigen for which an increase in immunogenicity is required and on the other hand, by systemic application, of increasing the immunological reactivity of the treated organism. Moreover, these compounds can enhance cellular as well as humoral immunity and activate lymphocytes responsible for the formation of antibodies.

The compounds of the present invention can consequently be employed as (1) adjuvants by mixing them with vaccines with the goal of improving the effectiveness of the vaccination and (2) protective agents against infections caused by viruses owing to immunity by humoral antibodies and/or to cellular mediation.

Moreover, one can equally utilize the new compounds without simultaneously supplying antigen in order to enhance immune reactions that are already taking place in a subliminal fashion in a mammalian host. These compounds are therefore especially indicated for stimulation of individual immune defense, e.g., at the time of chronic or acute infections or in cases of selective (antigen-specific) immunological deficiencies as well as in situations of immunedeficiency, but also acquired general deficiency (i.e., not antigen-specific) as appears with age, during initial shock from a grave illness, and before and soon after radiation therapy or immunosuppressive hormones. The said compounds can subsequently be administered in combination with anti-infectious antibiotics, chemical therapeutics or other methods of treatment, to combat immunological deficiencies. The described compounds are thus indicated equally for general prophylaxis of infectious disease in man and animal.

EXAMPLE 1

1,6-Dihydroxy-2,5-bis-(1-adamantanaminomethyl)-naphthalene dihydrochloride

Step A: 2:9-di-(1-Adamantyl)-1:2:3:4:7:8:9:10-octahydro-2:9-diaza-4:7-dioxachrysene To a mixture of 1-adamantanamine (7.6 g, 0.050 mol) and methanol (40 ml) cooled in an ice-bath were added with stirring 37% formaldehyde (wt. % solution in water, 8.1 ml, 0.10 mol) followed by a solution of 1,6-dihydroxynaphthalene (4.0 g, 0.025 mol) in methanol (25 ml). The reaction mixture was allowed to attain room temperature and was stirred overnight. The resulting solid was filtered and washed with methanol. Purification was achieved by vacuum filtration through a pad of silica gel (Merck #7734) and elution initially with dichloromethane and subsequently 100:1 and 25:1 dichloromethanediethyl ether; yield 6.8 g (53%); m/z (e.i.) 347 (M-163). The 90 MHz NMR spectrum in chloroform-d was in accord with the desired structure: $\delta$4.17 (s, 2H, $CH_2N$); 4.34 (s, 2H, $CH_2N$); 5.02 (s, 2H, $OCH_2N$); and 5.12 (s, 2H, $OCH_2N$).

Step B: 1,6-Dihydroxy-2,5-bis-(2-adamantanaminomethyl) naphthalene dihydrochloride A mixture of 2:9-di-(1-adamantyl)-1:2:3:4: 7:8:9:10-octahydro-2:9-diaza-4:7-dioxachrysene (4.5 g, 8.8 mmol), concentrated hydrochloric acid (50 ml) and 50% ethanol (1.6 L) was heated at reflux temperature for 48 hours, cooled, and evaporated under diminished pressure. The residue was triturated with isopropanol and diethyl ether to afford a solid that was filtered and recrystallized from 80% ethanol-diethyl ether; yield 3.0 g (61%); mass spectrum (fast atom bombardment): m/z 486 (free base). The 200 MHz NMR spectrum in methanol-$d_4$ was in accord with the desired structure: $\delta$4.38 (s, 2H, $CH_2N$); 4.65 (s, 2H, $CH_2N$); 7.29 (d, 1H, phenyl); 7.59 (m, 2H, phenyl); and 8.32 (d, 1H, phenyl).

EXAMPLE 2

1,6-Dihydroxy-2,5-bis-(cyclohexylmethylaminomethyl)naphthalene dihydrochloride

Step A: 2:9-di-(Cyclohexylmethyl)-1:2:3:4:7:8:9:10-octahydro-2:9-diaza-4:7-dioxachrysene Employing the procedure described in Step A of Example 1, but substituting for the 1-adamantanamine an equivalent amount of cyclohexylmethylamine, the product was obtained as a white solid after recrystallization from 1,4-dioxane. The 200 MHz NMR spectrum in chloroform-d was in accord with the desired structure: $\delta$2.60 (d, 4H, $N-CH_2$—); 4.06 (s, 2H, $CH_2N$); 4.26 (s, 2H, $CH_2N$); 4.90 (s, 2H, $OCH_2N$); 5.00 (s, 2H, $OCH_2N$); 7.00 (d, 1H, phenyl); 7.10 (dd, 2H, phenyl); and 7.97 (d, 1H, phenyl).

Step B: 1,6-Dihydroxy-2,5-bis-(cyclohexylmethylaminomethyl)-naphthalene dihydrochloride A mixture of 2:9-di-(cyclohexylmethyl)-1:2:3:4:7:8:9:10-octahydro-2:9-diaza-4:7-dioxachrysene (500 mg, 1.15 mmol), concentrated hydrochloric acid (2.55 ml) and 80% ethanol (50 ml) was heated at reflux temperature for 3 hours, cooled, and evaporated under diminished pressure. The residue was triturated with isopropanol-diethyl ether to give a solid that was filtered and recrystallized from 80% ethanol-diethyl ether; yield 210 mg (38%); mass spectrum (fast atom bombardment): m/z 411 (M). The 200 MHz NMR spectrum in methanol-$d_4$ was in accord with the desired structure: $\delta$2.93 (d, 2H, $N-CH_2$—); 2.98 (d, 2H, $N-CH_2$—); 4.42 (s, 2H, $CH_2N$); and 4.70 (s, 2H, $CH_2N$).

EXAMPLE 3

1,6-Dihydroxy-2,5-bis-(4-tert-butylcyclohexylaminomethyl)naphthalene dihydrochloride (mixture of isomers)

Step A: 2:9-di-(4-tert-Butylcyclohexyl)-1:2:3:4:7:8:9:10-octahydro-2:9-diaza-4:7-dioxachrysene To a mixture of 4-tert-butylcyclohexylamine (mixture of isomers) (9.7 g, 0.062 mol) and methanol (35 ml) cooled in ice bath were added with stirring 37% formaldehyde (wt. % solution in water, 10.0 ml, 0.12 mol) and subsequently a solution of 1,6-dihydroxynaphthalene (5.0 g, 0.031 mol) in methanol (25 ml). The bath was removed and the mixture was heated at reflux temperature for 1 hour and cooled. The solid Product was filtered and washed with methanol and diethyl ether. The solid was dissolved in the minimal amount of dichloromethane and vacuum filtered through a pad of silica gel (Merck #7734) and elution with 10:1 dichloromethane-diethyl ether. Thin layer chromatographic (tlc) investigation (1:1 hexane-diethyl ether) indicated isolation of a two-component mixture which was subjected to flash column chromatography on silica gel (elution with 10:1 hexane-diethyl ether). 90 MHz NMR spectral investigation (chloroform-d) of the thin layer more mobile product (1.2 g) indicated a mixture of isomers, whereas the less mobile product (1.3 g) to be a single isomer: 0.80 (s, 18H, $2xC(CH_3)_3$); $\delta$4.19 (s, 2H, $CH_2N$); 4.38 (s, 2H, $CH_2N$); 5.08 (s, 2H, $OCH_2N$); and 5.16 (s, 2H, $OCH_2N$).

Step B: 1,6-Dihydroxy-2,5-bis-(4-tert-butylcyclohexylaminomethyl)-naphthalene dihydrochloride (mixture of isomers)

A mixture of the faster-moving product from Step A above (1.0 g) and concentrated hydrochloric acid (2.5 ml) in 80% ethanol (100 ml) was heated at reflux temperature for 18 hours, cooled, and evaporated under diminished pressure. The residue was triturated with isopropanol-diethyl ether, and the resulting solid filtered, washed with ether, and dried in vacuo to give the product as a light tan solid; yield 0.95 g (87%). The 200 MHz NMR spectrum in methanol-$d_4$ indicated a mixture of isomers.

EXAMPLE 4

1,6-Dihydroxy-2,5-bis-(4-tert-butylcyclohexylaminomethyl)-naphthalene dihydrochloride (single isomer)

The slower-moving product from Step A of Example 3 (1.0 g) was treated with concentrated hydrochloric acid in aqueous ethanol and worked-up in a similar manner as that described in Step B of Example 3 to give the product as a white solid (300 mg), whose 200 MHz NMR spectrum in methanol-d$_4$ indicated a single isomer: $\delta$0.91 (s, 18H, 2x C(CH$_3$)$_3$); 4.43 (s, 2H, CH$_2$N); 4.70 (s, 2H, CH$_2$N); 7.31 (d, 1H phenyl); 7.62 (dd, 2H, phenyl); and 8.33 (d, 1H phenyl).

EXAMPLE 5

1,6-Dihydroxy-2,5-bis-(2-methylcyclohexylaminomethyl)naphthalene dihydrochloride (mixture of isomers)

Step A: 2:9-di-(2-Methylcyclohexyl)-1:2:3:4:7:8:9:10-octahydro-2:9-diaza-4:7-dioxachrysene Employing the procedure described in Step A of Example 1, but substituting for the 1-adamantanamine an equivalent amount of 2-methylcyclohexylamine (mixture of cis, trans isomers) and carrying out the reaction at room temperature for 18 hours, the title compound was obtained as an isomeric mixture that solidified upon trituration with hexane.

Step B: 1,6-Dihydroxy-2,5-bis-(2-methylcyclohexylaminomethyl)naphthalen dihydrochloride (mixture of isomers)

A mixture of 2:9-di-(2-methylcyclohexyl)-1:2:3:4:7:8:9:10-octahydro-2:9-diaza-4:7-dioxachrysene (0.80 g) and concentrated hydrochloric acid (2.5 ml) in 80% ethanol (50 ml) was heated at reflux temperature for 18 hours, cooled, and evaporated. The resulting solid was recrystallized from 80% ethanol-diethyl ether to afford the product (200 mg) as a mixture of cis, trans isomers (as indicated by the 200 MHz NMR spectrum in methanol-d$_4$); mass spectrum (fast atom bombardment): m/z 411 (M+H). N.m.r. data: $\delta$1.16 (d, 6H, 2×CH$_3$); 4.44 (m, 2H, CH$_2$N); and 4.70 (s, 2H, CH$_2$N).

EXAMPLE 6

1,6-Dihydroxy-2,5-bis-(3-methylcyclohexylaminomethyl)naohthalene dihydrochloride (mixture of isomers)

Employing the Procedure described in Example 5, but substituting for the 2-methylcyclohexylamine used in Step A thereof, an equivalent amount of 3-methylcyclohexylamine (mixture of cis, trans isomers), there were prepared in sequence:

Step A: 2:9-di-(3-Methylcyclohexyl)-1:2:3:4:7:8:9:10-octahydro-2:9-diaza-4:7-dioxachrysene The product was purified by chromatography 7 on a pad of silica gel (Merck #7734, packed as a slurry in 10:1 hexane-ether) and elution with 10:1 hexane-ether.

Step B: 1,6-Dihydroxy-2,5-b±s-(3-methylcyclohexylaminomethyl)-naphthalene dihydrochloride Obtained as a mixture of isomers as indicated by the 200 MHz NMR spectrum in methanol-d$_4$: $\delta$1.01 (d, 3H, CH$_3$-minor isomer); 1.02 (d, 3H, CH$_3$-major isomer); 4.42 (s, 2H, CH$_2$N); and 4.68 (s, 2H, CH$_2$N).

EXAMPLE 7

1,6-Dihydroxy-2,5-bis-(trans-4-methylcyclohexylaminomethyl)-naphthalene dihydrochloride Step A: 2:9-di-(trans-4-Methylcyclohexyl)-1:2:3:4:7:8:9:10-octahydro-2:9 diaza-4:7-dioxachrysene Starting from 1,6-dihydroxynaphthalene (10.0 g, 0.062 mol) and 4-methylcyclohexylamine (mixture of cis and trans isomers) (14.1 g, 0.124 mol), and following the procedure set forth in Step A of Example 1, initially an isomeric mixture (6.7 g) was obtained after vacuum filtration through a pad of silica gel (Merck #7734) and elution with 50:1 dichloromethane-diethyl ether. This mixture (5.7 g) was further chromatographed on a Waters Prep LC/system 500 using dual Prep-PAK ™ 500 silica columns with 5:1 hexane-ethyl acetate as the eluant. Two main fractions were collected; that containing the slower-moving component (2.5 g) was identified on the basis of its 200 MHz NMR spectrum in chloroform-d as the pure trans isomer: $\delta$0.84 (d, 6H, 2CH$_3$'S); 4.18 (s, 2H, CH$_2$N) 4.38 (s, 2H, CH$_2$N); 5.05 (s, 2H, OCH$_2$N); 5.16 (s, 2H, OCH$_2$N); 6.98 (d, 1H, phenyl); 7.14 (dd, 2H, phenyl); and 7.96 (d, 1H, phenyl).

Step B: 1,6-Dihydroxy-2,5-bis-(trans-4-methylcyclohexylaminomethyl)-naphthalene dihydrochloride The trans isomer from Step A above (500 mg) was treated with concentrated hydrochloric acid (1 ml) in 80% ethanol (30 ml) for 24 hours at reflux temperature, cooled, and evaporated. The solid was triturated with isopropanol, filtered, washed with isopropanol and diethyl ether and dried in vacuo; yield 475 mg (85%). The 200 MHz NMR spectrum in methanol-d$_4$ was in accord with the desired structure; $\delta$0.94 (d, 3H, CH$_3$); 0.95 (d, 3H, CH$_3$); 4.43 (s, 2H, CH$_2$N); 4.69 (s, 2H, CH$_2$N); 7 31 (d, 1H, phenyl); 7.62 (dd, 2H, phenyl); and 8.32 (d, 1H, phenyl); mass spectrum (fast atom bombardment): m/z 411 (M+H).

EXAMPLE 8

1,6-Dihydroxy-2,5-bis-(4-methoxycyclohexylaminomethyl)naphthalene dihydrochloride (mixture of isomers)

Employing the procedure described in Example 5, but substituting for the 2-methylcyclohexylamine used in Step A thereof, an equivalent amount of 4-methoxycyclohexylamine (mixture of cis and trans isomers), there were prepared in sequence:

Step A: 2:9-di-(4-Methoxycyclohexyl)-1:2:3:4:7:8:9:10-octahydro-2:9-diaza-4:7-dioxachrysene;

Step B: 1,6-Dihydroxy-2,5-bis-(4-methoxycyclohexylaminomethyl)-naphthalene dihydrochloride (mixture of isomers)-the 200 MHz NMR spectrum in methanol-d$_4$ indicated a mixture of cis and trans isomers

EXAMPLE 9

1,6-Dihydroxy-2,5-bis-(4-oxa-cyclohexylaminomethyl) naphthalene dihydrochloride Employing the procedure described in Example 5, but substituting for the 2-methylcyclohexylamine used in Step A thereof, an equivalent amount of 4-oxacyclohexylamine, there were prepared in sequence:

Step A: 2:9-di-(4-Oxa-cyclohexyl)-1:2:3:4:7:8:9:10-octahydro-2:9-diaza-4:7-dioxachrysene;

n.m.r. data (200 MHz, CDCl$_3$): $\delta$4.20 (s, 2H, CH$_2$N); 4.40 (s, 2H, CH$_2$N); 5.08 (s, 2H, OCH$_2$N); 5.18 (s, 2H, OCH$_2$N); 6.99 (d, 1H, phenyl); 7.14 (dd, 2H, phenyl);

and 7.96 (d, 1H, phenyl; mass spectrum (e.i.): m/z 410 (M).

Step B: 1,6-Dihydroxy-2,5-bis-(4-oxa-cyclohexylaminomethyl)-naphthalene dihydrochloride-the 200 MHz NMR spectrum in methanol-d$_4$ was in accord with the desired structure

EXAMPLE 10

1,6-Dimethoxy-2,5-bis-(cyclohexylaminomethyl)naphthalene dihydrochloride

Step A: 1,6-Dihydroxy-2,5-bis-(cyclohexylaminomethyl)-naphthalene

To a solution of 1,6-dihydroxy-2,5-bis- (cyclohexylaminomethyl)-naphthalene dihydrochloride (prepared by modification of the process set forth in U.S. Pat. No. 3,009,912) (5.0 g, 0.011 mol) in water (200 ml) was added 0.1 N sodium hydroxide (220 ml, 0.022 mol). The solid that separated out was collected by filtration, washed with water, and dried in vacuo; yield 4.0 g (95%). The 200 MHz NMR spectrum in chloroform-d was in accord with the desired structure. Mass spectrum(fast atom bombardment): m/z 383 (M+H).

Step B: 1,6-Di-benzyloxycarbonyloxy-2,5-bis-[N-(cyclohexyl)-benzyloxycarbonylaminomethyl]-naphthalene To a solution of 1,6-dihydroxy-2,5-bis-(cyclohexylaminomethyl)-naphthalene (3.8 g, 9.9 mmol) in dichloromethane (100 ml) were added, with cooling in an ice bath, triethylamine (6.9 ml, 50 mmol) and dropwise with stirring benzyl chloroformate (5.6 ml, 40 mmol). The reaction mixture was stirred at room temperature for 1 hour, diluted with ether, washed three times with water, dried (sodium sulfate) and evaporated to give the product as a thick syrup; yield 2.0 g.

Step C: 1,6-Dihydroxy-2,5-bis-[N-(cyclohexyl)-benzyloxycarbonylaminomethyl)-naphthalene A solution of the crude product from Step B (2.0 g, 2.3 mmol) in methanol (50 ml) was treated with sodium methoxide (120 mg, 2.2 mmol) for 18 hours at room temperature. The mixture was evaporated, the residue taken up in diethyl ether, acetic acid (1 ml) added, the solution washed three times with water, saturated aqueous sodium chloride solution, dried (sodium sulfate) and evaporated. The crude product was vacuum filtered through a column of silica gel (Merck #7734) eluted with 2:1 hexane-ether; yield 1.5 g.

Step D: 1,6-Dimethoxy-2,5-bis-[N-(cyclohexyl)-benzyloxycarbonylaminomethyl)-naphthalene To a suspension of sodium hydride (97%) (110 mg) in N,N-dimethylformamide (5 ml) was added dropwise under a nitrogen atmosphere a solution of 1,6-dihydroxy-2,5-bis-[N-(cyclohexyl)-benzyloxycarbonylaminomethyl)-naphthalene (1.0 g, 1.5 mmol) in N,N-dimethylformamide (5 ml). The reaction mixture was stirred at room temperature for 1 hour, at which time iodomethane (0.37 ml, 6.0 mmol) was added. The mixture was stirred at room temperature for an additional hour, poured into water, and extracted with diethyl ether. The combined extracts were washed three times with water, saturated aqueous sodium chloride solution, dried (sodium sulfate) and evaporated. The crude product was chromatographed on a column of silica gel (Merck #7734) that was eluted with dichloromethane. Fractions containing pure product were combined and evaporated to afford 1,6-dimethoxy-2,5-bis-[N-(cyclohexyl)-benzyloxycarbonylaminomethyl)-naphthalene; yield 360 mg (35%).

Step E: 1,6-Dimethoxy-2,5-bis-(cyclohexylaminomethyl)naphthalene

A solution of 1,6-dimethoxy-2,5-bis-[N-(cyclohexyl)-benzyloxycarbonylaminomethyl)-naphthalene (250 mg) in methanol (10 ml) was hydrogenated at atmospheric pressure in the presence of 5% palladium-on-charcoal (50 mg) for 2 hours at room temperature. The catalyst was removed by filtration through Celite, and the filtrate was evaporated to afford the product as a yellow syrup; yield 60 mg (37%).

Step F: 1,6-Dimethoxy-2,5-bis-(cyclohexylaminomethyl)naphthalene dihydrochloride To a solution of the free base (60 mg) in methanol (5 ml) was added a drop of concentrated hydrochloric acid. Ether was added until the product separated out as an oil. The mixture was evaporated and triturated with isopropanol and ether. The solid was filtered, washed with ether, and dried in vacuo: yield 50 mg (72%). The 200 MHz NMR spectrum in methanol-d$_4$ was in accord with the desired structure: δ4.06 (s, 3H, OCH$_3$); 4.14 (s, 3H, OCH$_3$); 4.44 (s, 2H, CH$_2$N); 4.74 (s, 2H, CH$_2$N); 7.70 (dd, 2H, phenyl); 8.02 (d, 1H, phenyl); and 8.40 (d, 1H, phenyl).

EXAMPLE 11

1,6-Di-(n-butyloxy)-2,5-bis-(cyclohexylaminomethyl)-naphthalene dihydrochloride

Employing the procedure described in Example 10, but substituting for the iodomethane used in Step D thereof, an equivalent amount of 1-iodobutane, there were prepared in sequence:

1,6-Di-(n-butyloxy)-2,5-bis-[N-(cyclohexyl)-benzyl- oxycarbonylaminomethyl)-naphthalene 1,6-Di-(n-butyloxy)-2,5-bis-(cyclohexylaminomethyl) naphthalene 1,6-Di-(n-butyloxy)-2,5-bis-(cyclohexylaminomethyl) naphthalene dihydrochloride; n.m.r. data (200 MHz, CD$_3$OD); δ4.10 (t, 2H, OCH$_2$); 4.36 (t, 2H, OCH$_2$); 4.44 (s, 2H, CH$_2$N); 4.74 (s, 2H, CH$_2$N); 7.64 (d, 1H, phenyl); 7.75 (d, 1H, phenyl); 8.02 (d, 1H, phenyl); and 8.36 (d, 1H, phenyl).

EXAMPLE 12

1,6-Dihydroxy-2,5-bis-(cyclopentylmethylaminomethyl)naphthalene dihydrochloride

Employing the procedure described in Example 5, but substituting for the 2-methylcyclohexylamine used in Step A thereof, an equivalent amount of aminomethylcyclopentane, there were prepared in sequence:

Step A: 2:9-di-(Cyclopentylmethyl)-1:2:3:4:7:8:9:10-octahydro-2:9-diaza-4;7-dioxachrysene Step B: 1,6-Dihydroxy-2,5-bis-(cyclopentylmethylaminomethyl)-naphthalene dihydrochloride

EXAMPLE 13

1,6-Dihydroxy-2,5-bis-(trans-2-methylcyclopentylaminomethyl)-naphthalene dihydrochloride Employing the procedure described in Example 5, but substituting for the 2-methylcyclohexylamine used in Step A thereof, an equivalent amount of trans-methylcyclopentylamine, there were prepared in sequence:

Step A: 2:9-di-(trans-2-methylcyclopentyl)-1:2:3:4:7:8:9:10-octahydro-2:9-diaza-4:7-dioxachrysene; n.m.r. data (200 MHz, CDCl$_3$): δ0.95 (d, 3H, CH$_3$); 0.97 (d, 3H, CH$_3$); 5.00 (s, 2H, OCH$_2$N); 5.10 (s, 2H, OCH₂N) 7.00 (d, 1H, phenyl); 7.14 (dd, 2H, phenyl); and 7.99 (d, 1H, phenyl).

Step B: 1,6-Dihydroxy-2,5-bis-(trans-2-methylcyclopentylaminomethyl)-naphthalene dihydrochloride; n.m.r data (200 MHz, CD₃OD): δ1.10 (d, 6H, 2 CH₃'s); 4.44 (m, 2H, CH₂N); 4.72 (s, 2H, CH₂N); 7.22 (d, 1H, phenyl); 7.65 (dd, 2H, phenyl); and 8.32 (d, 1H, phenyl).

EXAMPLE 14

In Vivo Immunopotentiation Against Challenge with Lethal Doses of Pseudomonas aeruginosa An immunocompromised mouse model, established by intraperitoneal treatment of random outbred albino CFl female mice (ca. 25g) with 250 mg/kg body weight of cyclophosphamide (CY) 4 days Prior to bacterial challenge with *Pseudomonas aeruginosa*, was used as the assay system. In this model, test compounds were injected only once (2 hours) after CY treatment. After bacterial challenge, LD₅₀'s (50% lethal doses) were determined. Increased LD₅₀'s in treated mice over controls indicated a return to normality. The LD₅₀ for untreated or vehicle-treated mice was routinely $10^6$–$10^7$ colony forming units (CFU) of *P. aeruginosa* organisms. After CY treatment, the LD₅₀ was reduced to $10^1$ to $10^2$ CFU's. The protection afforded by test compound (Protective Index) was determined by calculating the number of LD₅₀'s of protection of treated animals over the LD₅₀ of CY controls. Results are given below:

| Experiment # | Test Compound | Relative No. LD₅₀'s |
| --- | --- | --- |
| 1 | Example 2 | 320 |
| 2 | Example 3 | 2128 |
| 2 | Example 4 | 1000 |
| 3 | Example 5 | 133 |
| 3 | Example 6 | 151 |
| 4 | Example 7 | 1000 |

As is seen from the test results above, the compounds of the present invention provide for significant protection of the cyclophosphamide-immune compromised mouse against infection with a lethal challenge of *Pseudomonas aeruginosa*. Thus, for example, with the test compound of Example 4, the LD50 was raised by 1000-fold over untreated controls, indicating a return to the normal state for the host.

It is also reasonably believed that the disclosed compounds provide for significant protection in an immunocompromised human host against viral infections, and particularly in a human host that has been immunocompromised by an AIDS-related virus and is susceptible to a subsequent opportunistic infection by bacteria, fungus, or virus.

What is claimed is:

1. A composition for enhancing host resistance against bacterial, fungal or viral infection in a human host immunocompromised by AIDs-related virus comprising a compound of the formula:

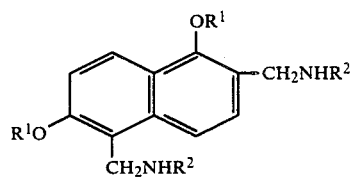

where $R^1$ is independently selected from H, $C_1$–$C_6$ alkyl; $R^2$ is independently selected from substituted monocycloalkyl, unsubstituted or substituted di- or tricycloalkyl, or substituted or unsubstituted tetrahydropyranyl, or pharmaceutically acceptable acid addition salts thereof, in combination with an anti-viral, anti-AIDS drug selected from the group consisting of ansamycin, ribavirin, deoxycytidine, HPA-23, AL-721, foscarnet and AZT, in a physiologically acceptable medium in an amount effective to impart enhanced resistance against opportunistic infection.

2. The compound of claim 1 wherein $R^2$ is selected from unsubstituted or substituted adamantyl; substituted cyclopentyl, cyclohexyl or cycloheptyl; unsubstituted or substituted tetrahydropyranyl or tetrahydrofurfuryl, and geometric isomers thereof.

3. The composition of claim 1 wherein said compound is of the formula:

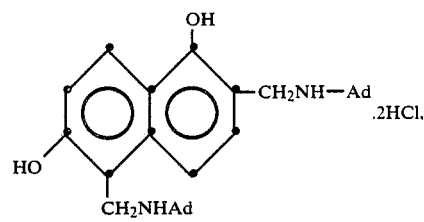

Where Ad is 1-adamantyl,

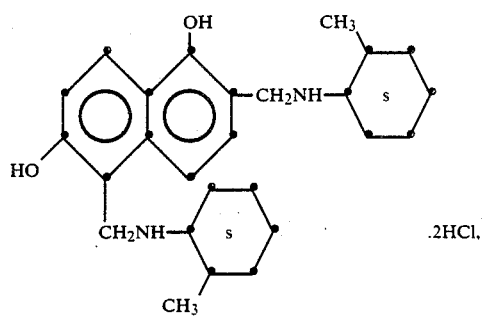

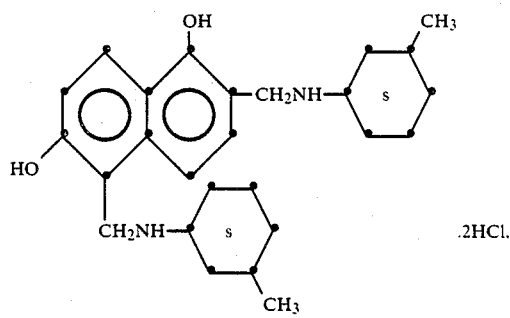

-continued
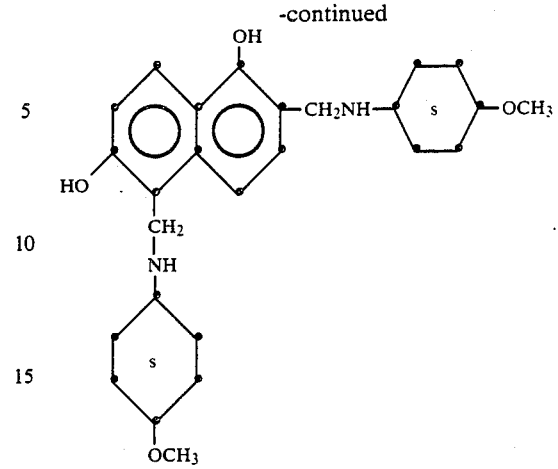
.2HCl.
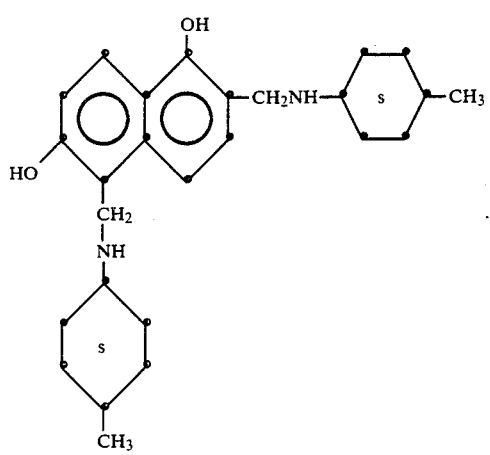
.2HCl,
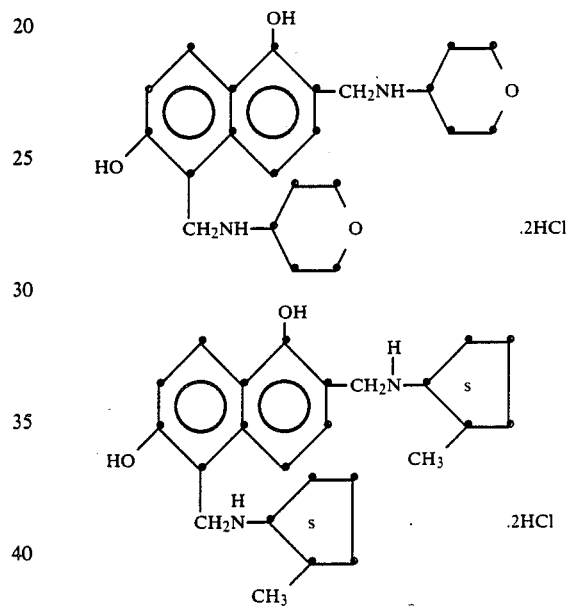
.2HCl
.2HCl
and cis, trans-isomers thereof.
* * * * *